US005722940A

United States Patent [19]
Gaylord, Jr. et al.

[11] Patent Number: 5,722,940
[45] Date of Patent: Mar. 3, 1998

[54] INDUSTRIAL BACK SUPPORT

[75] Inventors: John F. Gaylord, Jr.; R. Scott Gaylord, both of Matthews, N.C.

[73] Assignee: Medical Specialties, Inc., Charlotte, N.C.

[21] Appl. No.: 680,998

[22] Filed: Jul. 16, 1996

[51] Int. Cl.$^6$ .................................................. A61F 5/02
[52] U.S. Cl. .............................. 602/19; 128/96.1; 2/44
[58] Field of Search ........................ 602/19; 128/96.1, 128/99.1, 100.1, 101.1, 106.1, 107.1, 112.1, 113.1, 115.1; 2/44

[56] References Cited

U.S. PATENT DOCUMENTS

| | | | |
|---|---|---|---|
| 3,927,665 | 12/1975 | Wax | 602/19 |
| 4,245,628 | 1/1981 | Eichler | 602/19 |
| 4,696,291 | 9/1987 | Tyo | 602/19 |
| 4,794,916 | 1/1989 | Porterfield et al. | 602/19 |
| 5,012,798 | 5/1991 | Graf et al. | 602/19 |
| 5,207,636 | 5/1993 | Striano | 602/19 |
| 5,267,948 | 12/1993 | Elliott | 602/19 |
| 5,547,462 | 8/1996 | Lanigan et al. | 602/19 |

*Primary Examiner*—Jerome Donnelly
*Attorney, Agent, or Firm*—Bell Seltzer Intellectual Property Law Group of Alston & Bird, LLP

[57] ABSTRACT

A back support device for supporting a wearer's back during various activities is described. The back support device includes an inner belt, and outer substantially inelastic belt, and a semi-rigid abdominal plate positioned beneath the outer substantially inelastic belt. The back support device is designed to be positioned circumferentially about a wearer's waist or lower torso region, such that the abdominal plate overlies an abdominal region of the wearer, with the substantially inelastic belt securing the abdominal plate firmly in position thereon, in order to increase the intraabdominal pressure and thereby support the wearer's lower spine. The inner belt is desirably substantially elastic in order that it closely conforms to the wearer's body and assists in increasing the intraabdominal pressure. The back support device also desirably includes a lumbosacral pad, which can be positioned within a pocket located on a rear portion of the back support device, to thereby correspond with the wearer's lower spinal region and to provide effective contact between the inelastic belt of the device and the spine due to the spine's natural curvature in the lumbar region.

24 Claims, 2 Drawing Sheets

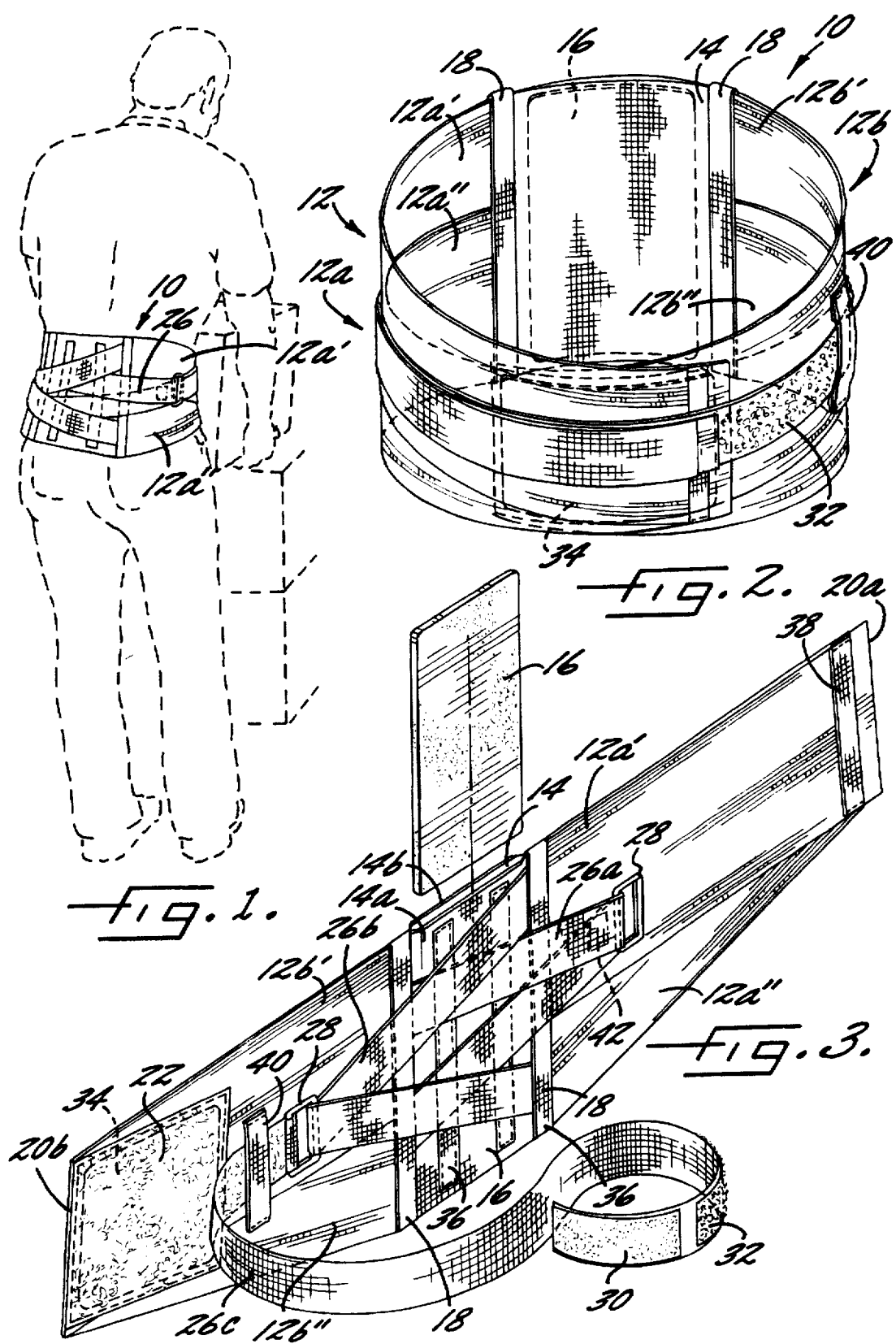

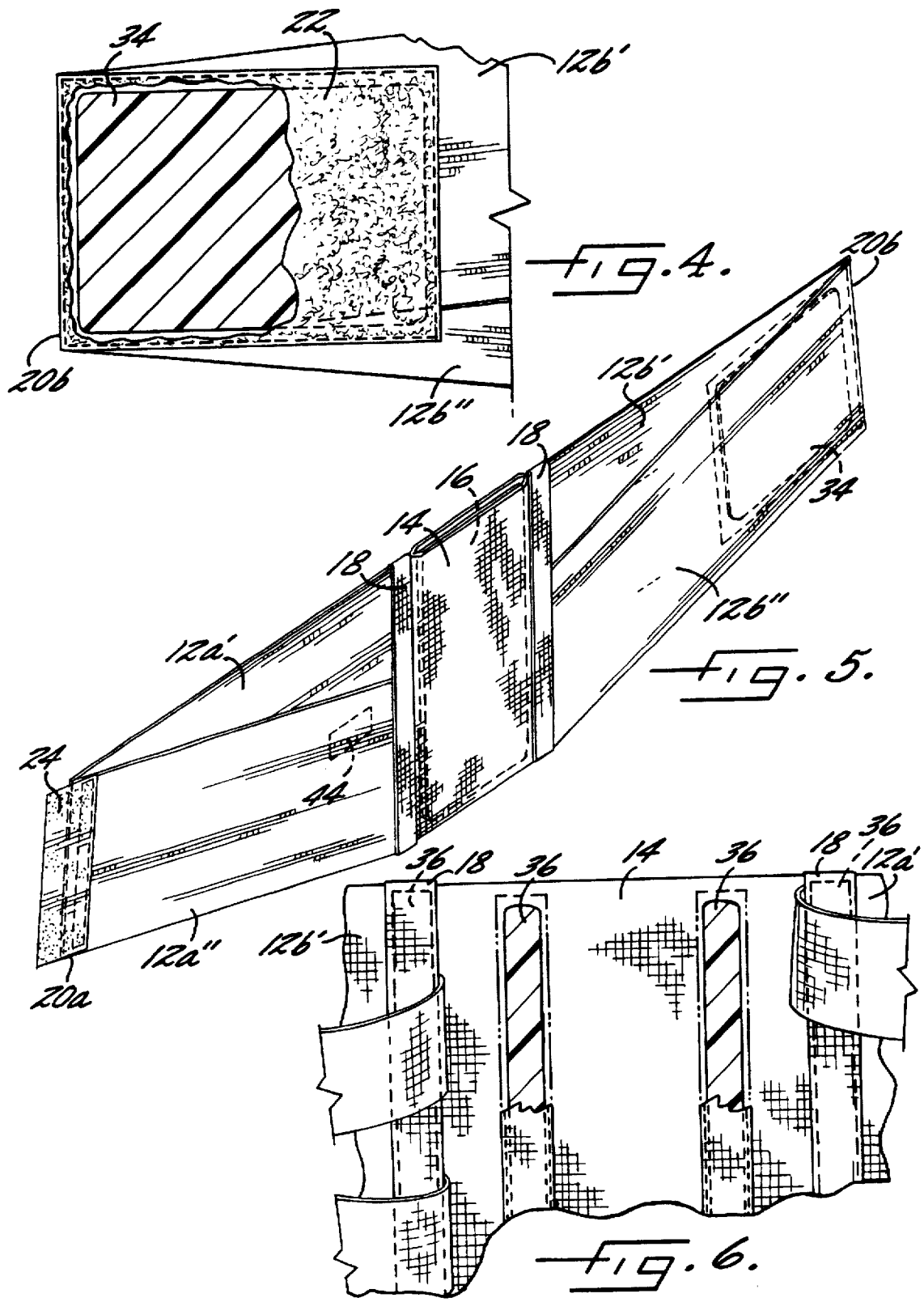

INDUSTRIAL BACK SUPPORT

BACKGROUND OF THE INVENTION

(1) Field of the Invention

The invention generally relates to an industrial back support, and more specifically, to an industrial back support which provides a concerted combination of abdominal and lower back support.

(2) Description of the Prior Art

Back injuries have become one of the leading causes of disability. At some point in their lives, most individuals will suffer from back pain of one sort or another; such pain can be long-lasting and debilitating for many people. The causes of back pain are varied: for some people, a one-time over-stressing of back muscles and ligaments can cause lasting pain. For others, the pain can be caused by naturally poor posture or by jobs or hobbies which require that they assume certain positions, in particular, for long periods of time. For still others, motions such as bending, lifting, and the like which are repeatedly performed can cause back discomfort, particularly when proper body alignment is not maintained throughout the motion.

To help reduce the occurrence of such injuries, federal workplace guidelines, as well as many employers, often require that employees engaged in particular jobs wear back support devices of some variety.

Examples of prior art back supports are described in U.S. Pat. Nos. 5,421,809, 5,388,274, and 4,475,543 to Rise, Glover et al., and Brooks et al., respectively. Each of these patents describes a support device which provides direct support for a wearer's spinal region through the provision of a pad proximate a wearer's lower back.

It has been found, however, that the abdominal muscles play a large part in the support of a person's spine, and thus the aforementioned supports, by only providing support to a wearer's spinal region, have failed to provide optimal back support for their wearers. Further, because the majority of the human waist region is fleshy, its configuration changes during certain motions, such as bending, due to muscle contraction and the like. Thus, because the aforementioned patents describe rigid support directly proximate the lower spine only, their effectiveness in supporting a person's back during certain motions can tend to be limited.

Several other patents describe supports which include some type of abdominal support, e.g. U.S. Pat. Nos. 5,433,697 and 5,105,806 to Woodhouse et al., and Cox, respectively. The patent to Woodhouse et al., describes the provision of a rigid abdominal pad for securement to a conventional leather-type weight lifting belt; thus the device would likely not provide the comfort and support levels desired for many uses. The patent to Cox describes a back brace having first and second substantially rigid dome-shaped support elements, one for positioning proximate a wearer's back and the other for positioning proximate his abdomen. The rigid support elements are secured together by first and second fastening belts. The support element for positioning proximate the wearer's abdomen is sized to extend across the full width of the front lower torso region of the wearer, and in a preferred form of the invention, it curves around the wearer's sides to some degree; thus it would limit user flexibility and could tend to irritate the prominences of the ilium (hip bones).

Thus, a need exists for an industrial back support device which provides an optimal amount of back support, yet is comfortable to wear.

SUMMARY OF THE INVENTION

With the foregoing in mind, it is therefore an object of the present invention to provide a back support device which provides proper support for a person's lumbar spine during various types of activities.

In addition, it is an object of the present invention to provide a back support device which encourages proper biomechanics during bending and lifting motions, and which is comfortable for the wearer.

The back support device according to the instant invention desirably includes an inner belt which is adapted to extend circumferentially about a wearer's waist or lower torso region. In a preferred form of the invention, the inner belt is substantially elastic (i.e. at least a portion of the belt is stretchable), such that the belt readily conforms to the wearer's body and provides some increase in intraabdominal pressure. Also in a preferred form of the invention, the inner belt tapers from a relatively greater width proximate the wearer's back to a relatively narrower width proximate the front of a wearer, in order that the belt comfortably conforms to the wearer's body.

An outer substantially inelastic belt is secured to the inner belt in an overlying relationship, so that the outer belt can be secured circumferentially about a wearer's waist region in a layered relationship with the inner belt. Because of its inelasticity, this outer belt is preferably narrower than the inner belt, in order that it will not be unduly constrictive or uncomfortable to the wearer. The inner belt can be formed from a single strip of material, or can be formed from a number of strips of material which cooperate to form the inner belt.

A semi-rigid abdominal plate is positioned on the back support device such that it will overlie a portion of a wearer's abdominal region when the support is positioned circumferentially about a wearer's waist region. The position of the semi-rigid abdominal plate on the back support device is also such that it will underlie at least a portion of the outer substantially inelastic belt. In this way, when the substantially inelastic belt is tightened about a wearer's waist, it biases the abdominal plate towards the wearer's abdominal region, to thereby increase the wearer's intraabdominal pressure. As a result, proper biomechanics are encouraged (i.e. the wearer's spine is supported in proper alignment.)

The semi-rigid abdominal plate is desirably sufficiently rigid that it distributes pressure applied by the substantially inelastic belt to the underlying portions of the wearer's body, but preferably possesses some flexibility in order that it will not be uncomfortable to the wearer. The abdominal plate also desirably has a relatively low profile in order that the device will be comfortable and its appearance will not be undesirably obtrusive, and has dimensions sized to cover a substantial portion of the wearer's abdominal region, yet avoid interference with any of the bony prominances of the ilium. In one embodiment of the invention, the abdominal plate is custom molded using conventional custom molding processes to accommodate the unique shape of the abdominal region of the wearer.

The back support device also preferably has a lumbosacral pad positioned on the device such that it corresponds to the lumbar (i.e. lower spinal) region of a wearer. This lumbosacral pad is adapted to fill the void located between the inelastic straps of the back support device and a wearer's spine which occurs as a result of the natural curvature of a person's spine and position of the adjacent musculature. This effective contact helps generate additional circumferencial force to further increase intraabdominal pressure. The lumbosacral pad can be selected to provide additional benefits; for example, a gel pack could be provided for applying hot and cold therapy to the wearer, or a custom molded plate could be provided to accommodate the unique shape of the lumbar region of the wearer. In a preferred form of the invention, a pocket is formed on the inner belt which is sized to receive such a lumbosacral pad; in this way, pads can be selectively interchanged or removed for heating, cooling, and molding.

The back support also desirably includes first and second substantially rigid stays which extend vertically along opposite sides of the pocket which receives the lumbosacral pad, to provide additional support for the wearer's back and for the back support device, and to reinforce the junctures of the pocket with the rest of the inner belt. Third and fourth stays are also desirably secured to the pocket itself, to provide greater rigidity to this area of the support. These stays can be formed from spring steel, hardened plastic, or the like.

In a preferred form of the invention, the pocket portion of the inner belt is made from substantially inelastic material, such as woven nylon. First and second elastic bands, which have a lesser vertical width than that of the pocket, are secured so that they extend straight outwardly from upper ends of the pocket structure. Because the elastic bands have a lesser width than the pocket structure, they terminate short of a lower end of the pocket. Third and fourth elastic bands, which are preferably of the same construction as the first and second elastic bands, are secured to opposite sides of the pocket structure proximate its lower end, such that they extend outwardly from the pocket structure at angles thereto and such that each of the third and fourth bands overlaps its adjacent first or second elastic band. In this way, the inner belt is made to have a tapered configuration so that the vertical width of the structure is less proximate the wearer's abdominal region than proximate the wearer's back.

The free end of each of the third and fourth bands is secured to the respective first or second band which it overlaps, and a first releasable fastener is secured to one of the band pairs while a cooperating fastener is secured to the other of the pairs. In this way, the inner belt can be readily and easily secured about a wearer's waist such that it conforms well thereto. Though described as being separate bands, it is noted that the first and third bands, and the second and fourth bands in like manner, could be formed from single pieces of elastic which are folded to form the respective straight and angled bands.

The semi-rigid abdominal plate is desirably secured to the inner band such that it will be centered over a wearer's abdomen when the back support is worn. The abdominal plate is desirably sewn in between the inner belt material and the releasable fastener secured thereon, which desirably is of the hook and loop variety.

As a result of the combination of inner and outer belts, the outer one of which is substantially inelastic, and the semi-rigid abdominal and lumbosacral plates working in concert, the intraabdominal pressure of the wearer is increased, and the lumbar region of the spine is desirably stabilized. Further, the tendency of a wearer to bend at the spine is discouraged, thereby encouraging proper biomechanics.

Other objects, features and advantages of the present invention will become apparent from the following detailed description when taken in conjunction with the accompanying drawings.

BRIEF DESCRIPTION OF THE DRAWINGS

FIG. 1 is an environmental perspective view of a back support device of the present invention, as it appears when worn by a person lifting a box;

FIG. 2 is a perspective view of a back support device according to the present invention, as it appears when the inner and outer belts are secured together to form a ring-shaped device for encircling a wearer's waist;

FIG. 3 is a partially exploded rear perspective view of a back support device according to the present invention as it appears when in extended form;

FIG. 4 is an enlarged view of an end of the device illustrated in FIG. 3, with a portion of fastener material removed to illustrate the position of the abdominal plate;

FIG. 5 is a front perspective view of the back support device illustrated in FIG. 3; and FIG. 6 is an enlarged view of a central portion of the back support device illustrated in FIG. 3.

DETAILED DESCRIPTION

With reference to the drawings, FIG. 1 illustrates a back support 10 according to the present invention as it appears when being worn by a person as he engages in the lifting of a box. As illustrated in FIGS. 2–6, the back support 10 includes an elongate inner belt 12 which includes a right band portion 12a and a left band portion 12b and which is sized to extend circumferentially about the waist or lower torso area of a wearer so as to fit the same closely and snugly. These band portions 12a, 12b are preferably made from a stretchable elastic material which is adapted to firmly fit around the wearer's lower torso or waist region.

In a preferred form of the invention, the right band portion 12a of the inner belt 12 is made from a single piece of material which is folded proximate its middle portion with the respective ends being offset from each other to form upper and lower band portion sections 12a', 12a". The left band portion 12b is desirably also produced in the same manner, to form band portion sections 12b' and 12b". In this way, the inner band can be made to taper from a wider back region to relatively narrower end portions 20a, 20b. It will be noted, however, that other types of bands could be used; for example, a single piece of tapered material could be used or band portion sections 12a', 12a" and 12b', 12b" could be formed from separate pieces of material and secured together in a conventional manner.

The inner belt 12 also desirably includes a lumbosacral pad receiving means proximate a central portion of the device. In a particularly preferred form of the invention, the lumbosacral pad receiving means is in the form of a pocket 14 which is located along a central portion of the elongate inner belt 12. In the embodiment of the invention illustrated in FIG. 3, the pocket 14 is formed from first and second pieces 14a, 14b of substantially nonstretchable material (e.g. woven nylon), while portions 12a, 12b are formed from wide bands of elastic. For example, it has been found that elastic bands approximately 4 to 6 inches in width perform well in the instant invention, though it is noted that other widths can be used within the scope of the invention. It is noted, however, that because the pocket portion 14 of the inner belt 12 represents only a minor portion of the overall belt, when this portion is made from a relatively nonstretchable material, the net effect is that the inner band is substantially elastic.

The pocket panels 14a, 14b are secured together and in turn secured to the respective right and left band portions 12a, 12b along juncture regions 18 by conventional methods such as sewing. In a preferred form of the invention, these juncture regions 18 are reinforced by way of webbing or strapping material as illustrated. Also in a preferred form of the invention the pocket 14 is adapted for easy removal of a lumbosacral support pad 16. For example, the upper end of the pocket 14 can be open, as illustrated. In this way, the type of support pad positioned within the back support 10 can be varied depending upon the needs of the wearer in a manner which will be discussed more fully herein.

Inner belt 12 also includes fastener means for securing the belt into a closed ring as illustrated in FIG. 2. In a preferred form of the invention, the securing means are located proximate the respective first and second ends 20a, 20b of the inner belt 12. In a particularly preferred form of the invention, the fastener means are of the hook and loop variety with one portion of the fastener being secured to the first end of the band 20a (as illustrated at 24 in FIG. 5) and a second piece of fastener material being secured proximate the second end 20b of the inner belt 12. It is noted, however, that other types of fasteners such as buckles, clips or the like could be used within the scope of the invention.

The back support 10 also includes a substantially inelastic outer belt 26. The inelastic outer belt 26 is desirably secured to the inner belt 12 in overlying fashion, such that the outer belt is positioned over the inner belt when the respective belts are secured about a wearer's waist. In a preferred form of the invention, the inelastic outer belt 26 has first and second halves 26a, 26b, one of which is secured to a third strap 26c. In a particularly preferred form of the invention, the first and second substantially inelastic outer belt halves 26a, 26b are each substantially V-shaped and formed of a single piece of strap material which is folded about its middle and the opposite ends of which are secured to the elastic inner band 12 as illustrated, for example, in FIG. 3.

In the embodiment illustrated, one of the folded inelastic outer belt halves extends over the other of the innerlastic outer belt halves proximate the pocket 14 such that the V-shapes overlap, in order that a greater amount of support is provided proximate the lumbar region of the wearer. In this form of the invention, a loop lock 28 is looped through each of the respective folded substantially V-shaped inelastic outer belt halves 26a, 26b, and the third strap 26c is secured to one of these loop locks. This strap 26c includes fastener means approximate its free end such that the belt can be wrapped circumferentially around a wearer's waist and the free end of strap 26c secured around a wearer's torso and secured to the loop lock 28 of the strap member to which it was not previously attached. In this form of the invention, the fasteners are desirably first and second hook and loop patches 30, 32. Though illustrated as being hook and loop patches, it is noted that any of a variety of conventional fastener means can be used such as buckles, clasps or the like; particularly preferred are fasteners which can be operated with one hand.

A semi-rigid abdominal plate 34 is positioned on the back support device 10 such that it will overlie an abdominal region of a wearer when the device is secured circumferentially about a wearer's waist. The abdominal plate is desirably made from a thermoplastic sheet material, thermoplastic foam, or a composite material, and desirably has a low profile in order to enhance the comfort of the support device and provide a desirable appearance. The material can be moldable, in order that a custom-molded abdominal plate can be provided. In a preferred form of the invention, the abdominal plate is about 0.02 to 0.5 inches thick. In a particularly preferred form of the invention, the abdominal plate is made from a 0.06 inch thick piece of polyethylene sheet material. The abdominal plate is also desirably semi-rigid, in order that it is capable of transferring forces from the inelastic outer belt 26 and thus increasing the intraabdominal pressure of the wearer. Further, it has been found that by using a semi-rigid material rather than a totally rigid material, wear comfort can be enhanced while a desirable level of performance is attained.

The abdominal plate 34 preferably is sized to cover substantially the entire abdominal region of a wearer, while avoiding contact with any of the bony protuberances of the ilium (hip bones), in order to provide a high degree of support (by maximizing the region where the intraabdominal pressure is increased) while minimizing the likelihood for wearer discomfort through contact of the abdominal plate with the wearer's bones. It has been found that abdominal plates on the order of 4–6 inches wide and 4–8 inches long, and more preferably about 5 inches wide by 5–7 inches long, perform well in the instant invention.

The semi-rigid abdominal plate 34 can be secured to the back support device 10 in any conventional manner such as by sewing, gluing, positioning it within a pocket, fastening it to either side of the inner belt, or the like. In a preferred form of the invention, the abdominal plate is positioned beneath the fastener material 22 located proximate the end 20b of the inner belt 12, and is captured between the fastener material and the inner belt when they are secured together.

As discussed previously, the lumbosacral pad 16 is also desirably provided to provide effective contact between the inelastic belt and the lumbar spine. The lumbosacral pad can be selected to provide additional benefits; for example, it can be a heatable or coolable gel type pad, a custom-molded pad, or a prefabricated non-customized pad. Various types of thermoplastic sheet material, foam materials, and composites can be used to produce the lumbosacral pad.

The back support device 10 also desirably includes a plurality of stays 36, which are positioned on the support substantially perpendicular to a longitudinal axis of the device, in order that they extend vertically when the device is donned by a wearer. In a preferred form of the invention, first and second stays are positioned on a central portion of the inner band 12 (and in the embodiment with a lumbosacral pad receiving pocket 14, on the pocket), while third and fourth stays are provided proximate the junctures 18 of the pocket and the right and left band portions 12a, 12b. The stays 36 provide additional support for the inner belt 12.

Also in a preferred form of the invention, various alignment accessories can be provided. For example, in the illustrated embodiment a strap guide 40 is provided for aligning the strap 26c relative to the inner belt 12, and mating alignment patches of hook and loop material 42, 44 are provided, one on strap 26a and the other on the inner belt, to encourage proper alignment of the strap. Also in a preferred form of the invention, a strap handle 38 is provided on the end 20a of the inner belt; the wearer can then position his or her hand in the handle to hold that end of the inner belt 12 while it is secured with the opposite end 20b in order that the belt can be secured snugly about the wearer's waist.

The materials used to manufacture each of the various parts of the back support device 10 can be selected by the manufacture according to cost considerations and the like. In a preferred form of the invention, the pocket 14 is formed from a woven nylon nylon material, while nylon seatbelt-type strapping material is used to form the inelastic belt 26.

The back support device is used as follows: an appropriate lumbosacral pad 16 is selected and secured within the pocket 14. The user then positions inner belt 12 about his waist snugly, centering the lumbosacral pad 16 (if provided) proximate the center of his back and the abdominal plate proximate his abdomen, and fastens the mating fasteners to secure the belt circumferentially about his waist. The user then secures the outer inelastic belt 26 circumferentially about his waist, such that the belt overlies the abdominal plate, and fastens the outer belt for a snug fit. In this way, the forces from the outer belt are distributed by the abdominal plate 34 to provide continuous and consistent pressure across the abdominal region, and thus increase the wearer's intraabdominal pressure. In addition, because of the location of the abdominal plate 34, biomechanically improper bending at the waist is rendered uncomfortable; thus the support device 10 encourages the wearer to bend properly (i.e. by flexing at the hips and knees), thereby reducing the chance of injury due to improper biomechanics.

In the drawings and specification there has been set forth a preferred embodiment of the invention, and although specific terms are employed, they are used in a generic and descriptive sense only and not for purposes of limitation, the scope of the invention being defined in the claims.

What claimed is:

1. A back support device comprising:
   an elongate elastic inner belt including a first fastener means for securing the belt about a waist of a wearer;
   an elongate substantially inelastic outer belt secured to said inner belt in a substantially overlying relationship thereto;
   a semi-rigid abdominal plate positioned beneath said substantially inelastic outer belt; and
   a second fastener means for securing said outer substantially inelastic belt circumferentially about a waist of a wearer in a substantially continuous overlying relationship with respect to the circumferential direction of said abdominal plate such that said inelastic outer belt biases the abdominal plate against an abdominal region of a wearer and said abdominal plate distributes pressure applied by the outer substantially inelastic belt to underlying regions of a wearer's body to thereby increase intraabdominal pressure and providing concerted support for the lumbar region of the spine.

2. The back support device according to claim 1, wherein said semi-rigid abdominal plate is sized to extend across substantially the entire abdominal region of a wearer, while avoiding any bony prominences of a wearer's hipbones.

3. The back support device according to claim 1, further comprising a lumbosacral pad positioned on said device and adapted to provide effective contact between the lumbar region of the spine of a wearer and the inelastic outer belt.

4. The back support device according to claim 1, wherein said inner belt is elastic, to conform closely to a wearer's body.

5. The back support device according to claim 1, further comprising a pocket positioned on said inner belt and adapted to receive a lumbosacral pad.

6. The back support device according to claim 1, wherein said abdominal plate is relatively wider than said substantially inelastic outer belt such that forces from said outer belt are distributed over regions of a wearer not covered by said outer belt by way of said abdominal plate.

7. The back support device according to claim 1, wherein said inner belt defines a longitudinal axis and further comprising a plurality of stays positioned substantially perpendicular to said longitudinal axis such that said stays extend vertically when said inner belt is positioned circumferentially about a wearer's waist.

8. A back support device for supporting a wearer's lower back and encouraging proper biomechanics comprising:
   an elongate elastic inner belt including fastening means for securing said belt circumferentially about a person's waist;
   a lumbosacral pad receiving means positioned proximate a central portion of said inner belt;
   a semi-rigid abdominal plate positioned on said inner belt remote from said lumbosacral pad receiving means and adapted to overlie a wearer's abdominal region when said inner belt is positioned circumferentially about a person's waist, and
   a substantially inelastic outer belt connected to the inner belt and including fastening means operatively connecting ends of the outer belt together for securing and tensioning said belt circumferentially about a wearer's waist, said outer belt being secured to said inner belt such that said outer belt substantially continuously overlies said semi-rigid abdominal plate in the circumferential direction when said inner and outer belts are positioned to extend circumferentially about a wearer's waist, such that said substantially inelastic outer belt biases the abdominal plate against an abdominal region of a wearer and said abdominal plate distributes pressure applied by the outer substantially inelastic outer belt to underlying regions of a wearer's body, to increase intraabdominal pressure.

9. The back support device according to claim 8, wherein said inner belt is elastic and said outer belt is relatively narrower than said inner belt and said abdominal plate, such that forces from said outer belt are distributed over regions of a wearer not covered by the outer belt by said abdominal plate.

10. The back support device according to claim 8, wherein said abdominal plate comprises a plastic material and is approximately 0.02–0.5 of an inch thick.

11. The back support device according to claim 8, further comprising a lumbosacral pad positioned proximate said lumbosacral pad receiving means to provide effective contact between the inelastic outer belt of the support device and a wearer's lumbar spine.

12. The back support device according to claim 11, wherein said lumbosacral pad is made from a moldable plastic material.

13. The back support device according to claim 11, wherein said lumbosacral pad comprises a gel pad.

14. The back support device according to claim 8, wherein said semi-rigid abdominal plate is sized to extend across substantially the entire abdominal region of a wearer, while avoiding any bony prominences of a wearer's hipbones.

15. The back support device according to claim 8, wherein said semi-rigid abdominal plate comprises a moldable plastic material.

16. A back support device for supporting a wearer's lower back comprising:
   an elongate substantially elastic inner belt including fastening means for securing said belt circumferentially about a person's waist, said inner belt tapering from a central relatively wider portion to first and second relatively narrower end portions;
   a lumbosacral pad positioned proximate said central relatively wider portion of said inner belt for filling void space proximate a wearer's lumbar region;
   a semi-rigid abdominal plate positioned on said inner belt proximate one of said first and second end portions; and
   a substantially inelastic outer belt connected to the inner belt and having opposite ends, said outer belt including fastening means operatively connecting the ends of the outer belt together for securing said outer belt circumferentially about a wearer's waist, said outer belt being relatively narrower than said inner belt and being secured on said inner belt such that when the inner and outer belts are positioned to extend circumferentially about a wearer's waist, the outer belt overlies an entire circumferential dimension of the abdominal plate and thereby biases the abdominal plate toward an underlying region of a wearer's body such that said abdominal plate distributes pressure applied by the outer belt to underlying portions of a wearer's body.

17. The back support device according to claim 16, wherein said substantially inelastic outer belt comprises first and second belt strap portions which cooperate to form the outer belt, said first and second belt strap portions being secured to said inner belt such that one overlaps the other proximate the lumbosacral pad, to thereby provide support for an underlying region of a wearer's body.

18. The back support device according to claim 16, wherein said semi-rigid abdominal plate has a length of about 4–8 inches, a width of about 4–6 inches, and a thickness of about 0.02–0.5 inches, to thereby provide a semi-rigid plate which covers the abdominal region of a wearer without interfering with any bony prominences of a wearer's hip bones.

19. The back support device according to claim 16, further comprising a handle positioned proximate one of said first and second end portions of said inner belt for assisting a wearer in donning the device.

20. The back support device according to claim 16, wherein said inner belt includes right and left band portions, each of which includes first and second band portion sections which are positioned in an overlapping relationship at an angle with respect to each other such that said inner belt tapers from said central relatively wider portion to said first and second relatively narrower end portions.

21. The back support device according to claim 16, wherein said semi-rigid abdominal plate comprises a moldable plastic material.

22. The back support according to claim 1, wherein said outer belt comprises two straps which are directly connectable to each other so as to thereby completely encircle a wearer's waist.

23. The back support according to claim 1, wherein said semi-rigid abdominal plate has a widthwise dimension which is perpendicular to the circumferential direction of the inner belt, and wherein the outer belt is positioned to overlie a medial portion of the widthwise dimension of the plate.

24. The back support according to claim 1, wherein said inner belt has opposite end portions of a predetermined widthwise extent, and wherein said semi-rigid plate has a widthwise extent which is substantially equal to the widthwise extent of the opposite end portions.

* * * * *